(12) United States Patent
Rudnic et al.

(10) Patent No.: US 7,282,221 B2
(45) Date of Patent: *Oct. 16, 2007

(54) ANTIVIRAL PRODUCT, USE AND FORMULATION THEREOF

(75) Inventors: Edward M. Rudnic, Potomac, MD (US); James D. Isbister, Potomac, MD (US); Donald J. Treacy, Jr., Woodbine, MD (US); Sandra E. Wassink, Frederick, MD (US)

(73) Assignee: Middlebrook Pharmaceuticals, Inc., Germantown, MD (US)

( * ) Notice: Subject to any disclaimer, the term of this patent is extended or adjusted under 35 U.S.C. 154(b) by 71 days.

This patent is subject to a terminal disclaimer.

(21) Appl. No.: 11/273,661

(22) Filed: Nov. 14, 2005

(65) Prior Publication Data

US 2006/0110455 A1    May 25, 2006

Related U.S. Application Data

(63) Continuation of application No. 10/288,000, filed on Nov. 5, 2002, now Pat. No. 6,984,401, which is a continuation of application No. 09/791,906, filed on Feb. 22, 2001, now Pat. No. 6,541,014, which is a continuation-in-part of application No. 09/687,237, filed on Oct. 13, 2000, now abandoned.

(51) Int. Cl.
*A61K 9/14* (2006.01)
*A61K 9/00* (2006.01)
*A61K 9/48* (2006.01)
*A61K 9/20* (2006.01)
*A61K 9/16* (2006.01)

(52) U.S. Cl. .................. 424/489; 424/400; 424/451; 424/464; 424/490; 424/497; 424/502

(58) Field of Classification Search ................ 424/489, 424/464
See application file for complete search history.

(56) References Cited

U.S. PATENT DOCUMENTS

| | | | |
|---|---|---|---|
| 3,108,046 A | 10/1963 | Harbit ........................ 167/82 |
| 3,870,790 A | 3/1975 | Lowey et al. .................. 424/19 |
| 4,007,174 A | 2/1977 | Laundon .................... 260/243 |
| 4,008,246 A | 2/1977 | Ochiai et al. ............. 260/306.8 |
| 4,018,918 A | 4/1977 | Ayer et al. .................... 514/24 |
| 4,048,306 A | 9/1977 | Maier et al. ................ 424/180 |
| 4,131,672 A | 12/1978 | Huffman ..................... 514/204 |
| 4,175,125 A | 11/1979 | Huffman ..................... 514/208 |
| 4,226,849 A | 10/1980 | Schor .......................... 424/19 |
| 4,236,211 A | 11/1980 | Arvesen ....................... 435/32 |
| 4,250,166 A | 2/1981 | Maekawa et al. ............. 424/81 |
| 4,331,803 A | 5/1982 | Watanabe et al. ............ 536/7.2 |
| 4,362,731 A | 12/1982 | Hill ............................ 424/256 |
| 4,369,172 A | 1/1983 | Schor et al. .................. 424/19 |
| 4,399,151 A | 8/1983 | Sjoerdsma et al. .......... 514/564 |
| 4,430,495 A | 2/1984 | Patt et al. .................. 536/16.3 |
| 4,435,173 A | 3/1984 | Siposs et al. ............... 609/155 |
| 4,474,768 A | 10/1984 | Bright ........................ 424/180 |
| 4,517,359 A | 5/1985 | Kobrehel et al. ............ 536/7.4 |
| 4,525,352 A | 6/1985 | Cole et al. .................. 424/114 |
| 4,529,720 A | 7/1985 | Cole et al. .................. 514/191 |
| 4,560,552 A | 12/1985 | Cole et al. .................. 424/114 |
| 4,568,741 A | 2/1986 | Livingston ................. 536/16.5 |
| 4,598,045 A | 7/1986 | Masover et al. .............. 435/34 |
| 4,616,008 A | 10/1986 | Hirai et al. .................. 514/200 |
| 4,634,697 A | 1/1987 | Hamashima ................ 514/202 |
| 4,644,031 A | 2/1987 | Lehmann et al. ........... 524/501 |
| 4,670,549 A | 6/1987 | Morimoto et al. ........... 536/7.4 |
| 4,672,109 A | 6/1987 | Watanabe et al. ............ 536/7.2 |
| 4,680,386 A | 7/1987 | Morimoto et al. ........... 536/7.4 |
| 4,710,565 A | 12/1987 | Livingston et al. ......... 536/16.5 |
| 4,723,958 A | 2/1988 | Pope et al. ............... 604/890.1 |
| 4,728,512 A | 3/1988 | Mehta et al. ................ 424/458 |
| 4,749,568 A | 6/1988 | Reusser et al. ............. 424/119 |
| 4,755,385 A | 7/1988 | Etienne et al. .............. 424/154 |
| 4,775,751 A | 10/1988 | McShane .................... 540/230 |
| 4,794,001 A | 12/1988 | Mehta et al. ............... 424/458 |
| 4,808,411 A | 2/1989 | Lu et al. ..................... 424/441 |
| 4,812,561 A | 3/1989 | Hamashima et al. ........ 540/222 |

(Continued)

FOREIGN PATENT DOCUMENTS

EP        0052075       11/1981

(Continued)

OTHER PUBLICATIONS

Bahmuller, Metabolites of Microorganisms. 248. Synthetic Analogs of Saphenamycin, J. Antibiot (Tokyo). Nov. 1998; 41(11): 1552-60.

(Continued)

*Primary Examiner*—Humera N Sheikh
(74) *Attorney, Agent, or Firm*—Elliot M. Olstein; Raymond E. Stauffer

(57) ABSTRACT

An antiviral product is comprised of at least three dosages forms, each of which has a different release profile, with the $C_{max}$ for the antiviral product being reached in less than about twelve hours. In one embodiment, there is an immediate release dosage form, as well as two or more delayed release dosage forms, with each of the dosage forms having a different release profile, wherein each reaches a $C_{max}$ at different times.

45 Claims, No Drawings

U.S. PATENT DOCUMENTS

| | | | |
|---|---|---|---|
| 4,828,836 A | 5/1989 | Elger et al. | 424/419 |
| 4,831,025 A | 5/1989 | Godtfredsen et al. | 514/195 |
| 4,835,140 A | 5/1989 | Smith et al. | 514/24 |
| 4,842,866 A | 6/1989 | Horder et al. | 424/468 |
| 4,849,515 A | 7/1989 | Matier et al. | 536/16.5 |
| 4,879,135 A | 11/1989 | Greco et al. | 623/1.48 |
| 4,894,119 A | 1/1990 | Baron, Jr. et al. | 162/168.2 |
| 4,895,934 A | 1/1990 | Matier et al. | 536/16.5 |
| 4,904,476 A | 2/1990 | Mehta et al. | 424/456 |
| 4,915,953 A | 4/1990 | Jordan et al. | 424/473 |
| 4,945,080 A | 7/1990 | Lindstrom et al. | 514/29 |
| 4,945,405 A | 7/1990 | Hirota | 358/516 |
| 4,971,805 A | 11/1990 | Kitanishi et al. | 424/494 |
| 4,990,602 A | 2/1991 | Morimoto et al. | 536/7.4 |
| 5,011,692 A | 4/1991 | Fujioka et al. | 424/426 |
| 5,045,533 A | 9/1991 | Philippe et al. | 514/29 |
| 5,051,262 A | 9/1991 | Panoz et al. | 424/468 |
| 5,110,597 A | 5/1992 | Wong et al. | 424/438 |
| 5,110,598 A | 5/1992 | Kwan et al. | 424/438 |
| 5,143,661 A | 9/1992 | Lawter et al. | 264/4.3 |
| 5,158,777 A | 10/1992 | Abramowitz et al. | 424/458 |
| 5,178,874 A | 1/1993 | Kwan et al. | 424/438 |
| 5,182,374 A | 1/1993 | Tobkes et al. | 536/16.5 |
| 5,204,055 A | 4/1993 | Sachs et al. | 419/2 |
| 5,213,808 A | 5/1993 | Bar-Shalom et al. | 424/473 |
| 5,229,131 A | 7/1993 | Amidon et al. | 424/451 |
| 5,230,703 A | 7/1993 | Alon | 604/20 |
| 5,274,085 A | 12/1993 | Amano et al. | 536/7.4 |
| 5,288,503 A | 2/1994 | Wood et al. | 424/497 |
| 5,334,590 A | 8/1994 | DiNinno et al. | 514/210.09 |
| 5,340,656 A | 8/1994 | Sachs et al. | 428/546 |
| 5,358,713 A | 10/1994 | Shimamura | 424/729 |
| 5,387,380 A | 2/1995 | Cima et al. | 264/69 |
| 5,393,765 A | 2/1995 | Infeld et al. | 514/365 |
| 5,395,626 A | 3/1995 | Kotwal et al. | 424/472 |
| 5,395,628 A | 3/1995 | Noda et al. | 424/490 |
| 5,399,723 A | 3/1995 | Iinuma et al. | 549/403 |
| 5,401,512 A | 3/1995 | Rhodes et al. | 424/458 |
| 5,413,777 A | 5/1995 | Sheth et al. | 424/490 |
| 5,414,014 A | 5/1995 | Schneider et al. | 514/535 |
| 5,422,343 A | 6/1995 | Yamamoto et al. | 514/29 |
| 5,430,021 A | 7/1995 | Rudnic et al. | 514/14 |
| 5,445,829 A | 8/1995 | Paradissis et al. | 424/480 |
| 5,457,187 A | 10/1995 | Gmeiner et al. | 536/25.5 |
| 5,462,747 A | 10/1995 | Radebaugh et al. | 424/465 |
| 5,466,446 A | 11/1995 | Stiefel et al. | 424/78.37 |
| 5,472,708 A | 12/1995 | Chen | 424/451 |
| 5,476,854 A | 12/1995 | Young | 514/254 |
| 5,490,962 A | 2/1996 | Cima et al. | 264/22 |
| 5,508,040 A | 4/1996 | Chen | 424/451 |
| 5,518,680 A | 5/1996 | Cima et al. | 264/401 |
| 5,538,954 A | 7/1996 | Koch et al. | 514/53 |
| 5,543,417 A | 8/1996 | Waldstreicher | 514/284 |
| 5,556,839 A | 9/1996 | Greene et al. | 514/29 |
| 5,567,441 A | 10/1996 | Chen | 424/494 |
| 5,576,022 A | 11/1996 | Yang et al. | 424/472 |
| 5,578,713 A | 11/1996 | McGill, III | 536/18.5 |
| 5,599,557 A | 2/1997 | Johnson et al. | 424/500 |
| 5,607,685 A | 3/1997 | Cimbollek et al. | 424/422 |
| 5,633,006 A | 5/1997 | Catania et al. | 424/441 |
| 5,672,359 A | 9/1997 | Digenis et al. | 424/463 |
| 5,688,516 A | 11/1997 | Raad et al. | 424/409 |
| 5,702,895 A | 12/1997 | Matsunaga et al. | 435/6 |
| 5,705,190 A | 1/1998 | Broad et al. | 424/465 |
| 5,707,646 A | 1/1998 | Yajima et al. | 424/439 |
| 5,719,132 A | 2/1998 | Lin et al. | 514/50 |
| 5,719,272 A | 2/1998 | Yang et al. | 536/7.4 |
| 5,725,553 A | 3/1998 | Moenning | 606/213 |
| 5,733,886 A | 3/1998 | Baroody et al. | 514/24 |
| 5,756,473 A | 5/1998 | Liu et al. | 514/29 |
| 5,780,446 A | 7/1998 | Ramu | 514/34 |
| 5,789,584 A | 8/1998 | Christensen et al. | 540/227 |
| 5,808,017 A | 9/1998 | Chang | 536/7.4 |
| 5,817,321 A | 10/1998 | Alakhov et al. | 424/400 |
| 5,827,531 A | 10/1998 | Morrison et al. | 424/450 |
| 5,837,284 A | 11/1998 | Mehta et al. | 424/459 |
| 5,837,829 A | 11/1998 | Ku | 536/7.4 |
| 5,840,329 A * | 11/1998 | Bai | |
| 5,840,760 A | 11/1998 | Carraher, Jr. et al. | 514/493 |
| 5,844,105 A | 12/1998 | Liu et al. | 536/18.5 |
| 5,849,776 A | 12/1998 | Czernielewski et al. | 514/398 |
| 5,852,180 A | 12/1998 | Patel | 536/7.4 |
| 5,858,986 A | 1/1999 | Liu et al. | 514/29 |
| 5,864,023 A | 1/1999 | Ku et al. | 536/7.2 |
| 5,869,170 A | 2/1999 | Cima et al. | 428/304.4 |
| 5,872,104 A | 2/1999 | Vermeulen et al. | 514/29 |
| 5,872,229 A | 2/1999 | Liu et al. | 536/18.6 |
| 5,877,243 A | 3/1999 | Sarangapani | 524/139 |
| 5,883,079 A | 3/1999 | Zopf et al. | 514/25 |
| 5,892,008 A | 4/1999 | Ku et al. | 536/18.5 |
| 5,910,322 A | 6/1999 | Rivett et al. | 424/484 |
| 5,919,219 A | 7/1999 | Knowlton | 607/102 |
| 5,919,489 A | 7/1999 | Saleki-Gerhardt et al. | 424/501 |
| 5,919,916 A | 7/1999 | Gracey et al. | 536/7.2 |
| 5,929,219 A | 7/1999 | Hill | 536/7.2 |
| 5,932,710 A | 8/1999 | Liu et al. | 536/18.7 |
| 5,945,124 A | 8/1999 | Sachs et al. | 424/472 |
| 5,945,405 A | 8/1999 | Spanton et al. | 514/29 |
| 5,972,373 A | 10/1999 | Yajima et al. | 424/439 |
| 5,980,942 A | 11/1999 | Katzhendler et al. | 424/465 |
| 5,985,643 A | 11/1999 | Tomasz et al. | 435/243 |
| 5,998,194 A | 12/1999 | Summers, Jr. et al. | 435/252.33 |
| 6,008,195 A | 12/1999 | Selsted | 514/14 |
| 6,010,718 A | 1/2000 | Al-Razzak et al. | 424/464 |
| 6,013,507 A | 1/2000 | Tomasz et al. | 435/252.3 |
| 6,027,748 A | 2/2000 | Conte et al. | 424/458 |
| 6,031,093 A | 2/2000 | Cole et al. | 540/349 |
| 6,048,977 A | 4/2000 | Cole et al. | 540/349 |
| 6,051,255 A | 4/2000 | Conley et al. | 424/482 |
| 6,051,703 A | 4/2000 | Cole et al. | 514/210.06 |
| 6,057,291 A | 5/2000 | Hancock et al. | 514/12 |
| 6,059,816 A | 5/2000 | Moenning | 606/213 |
| 6,063,613 A | 5/2000 | De Lencastre et al. | 435/252.3 |
| 6,063,917 A | 5/2000 | Ascher et al. | 540/217 |
| 6,068,859 A | 5/2000 | Curatolo et al. | 424/490 |
| 6,110,925 A | 8/2000 | Williams et al. | 514/272 |
| 6,117,843 A | 9/2000 | Baroody et al. | 514/24 |
| 6,120,803 A | 9/2000 | Wong et al. | 424/473 |
| 6,127,349 A | 10/2000 | Chasalow | 514/77 |
| 6,132,768 A | 10/2000 | Sachs et al. | 424/458 |
| 6,132,771 A | 10/2000 | Depui et al. | 424/468 |
| 6,136,587 A | 10/2000 | Tomasz et al. | 435/252.3 |
| 6,156,507 A | 12/2000 | Hiramatsu et al. | 435/6 |
| 6,159,491 A | 12/2000 | Durrani | 424/430 |
| 6,162,925 A | 12/2000 | Williams et al. | 548/335.5 |
| 6,183,778 B1 | 2/2001 | Conte et al. | 424/472 |
| 6,187,768 B1 | 2/2001 | Welle et al. | 514/199 |
| 6,214,359 B1 | 4/2001 | Bax | 424/400 |
| 6,218,380 B1 | 4/2001 | Cole et al. | 514/210.06 |
| 6,228,398 B1 | 5/2001 | Devane et al. | 424/484 |
| 6,231,875 B1 | 5/2001 | Sun et al. | 424/401 |
| 6,248,363 B1 | 6/2001 | Patel et al. | 424/497 |
| 6,251,647 B1 | 6/2001 | De Lencastre et al. | 435/193 |
| 6,265,394 B1 | 7/2001 | Sterzycki et al. | 514/203 |
| 6,270,805 B1 | 8/2001 | Chen et al. | 424/497 |
| 6,280,771 B1 | 8/2001 | Monkhouse et al. | 424/484 |
| 6,294,199 B1 | 9/2001 | Conley et al. | 424/468 |
| 6,294,526 B1 | 9/2001 | Higuchi et al. | 514/192 |
| 6,296,873 B1 | 10/2001 | Katzhendler et al. | 424/465 |
| 6,297,215 B1 | 10/2001 | Hancock et al. | 514/12 |
| 6,299,903 B1 | 10/2001 | Rivett et al. | 424/464 |
| 6,306,436 B1 | 10/2001 | Chungi et al. | 424/464 |
| 6,309,663 B1 | 10/2001 | Patel et al. | 424/450 |
| 6,322,819 B1 | 11/2001 | Burnside et al. | 424/494 |

| | | | | | | |
|---|---|---|---|---|---|---|
| 6,333,050 B2 | 12/2001 | Wong et al. ............... 424/473 | | 6,767,899 B1 | 7/2004 | Kay et al. .................. 514/62 |
| 6,340,475 B2 | 1/2002 | Shell et al. ............... 424/469 | | 6,777,420 B2 | 8/2004 | Zhi et al. ................. 514/272 |
| 6,352,720 B2 | 3/2002 | Martin et al. ............. 424/464 | | 6,783,773 B1 | 8/2004 | Storm et al. ............. 424/468 |
| 6,358,525 B1* | 3/2002 | Guo et al. | | 6,818,407 B2 | 11/2004 | Hancock et al. ........... 435/7.1 |
| 6,358,528 B1 | 3/2002 | Grimmett et al. ......... 424/474 | | 6,824,792 B2 | 11/2004 | Foreman et al. .......... 424/487 |
| 6,383,471 B1 | 5/2002 | Chen et al. ................ 424/45 | | 6,872,407 B2 | 3/2005 | Notario et al. ............ 424/464 |
| 6,384,081 B2 | 5/2002 | Berman .................... 514/621 | | 6,878,387 B1 | 4/2005 | Petereit et al. ............ 424/490 |
| 6,391,614 B1 | 5/2002 | Tomasz et al. ........... 435/253.2 | | 6,906,035 B2 | 6/2005 | Hancock et al. ............ 514/12 |
| 6,399,086 B1 | 6/2002 | Katzhendler et al. ...... 424/405 | | 6,929,804 B2 | 8/2005 | Rudnic et al. ............. 424/468 |
| 6,403,569 B1 | 6/2002 | Achterrath ................ 514/50 | | 6,946,458 B2 | 9/2005 | Turos ..................... 514/210.15 |
| 6,406,717 B2 | 6/2002 | Cherukuri ................ 424/484 | | 6,984,401 B2 | 1/2006 | Rudnic et al. ............. 424/489 |
| 6,406,880 B1 | 6/2002 | Thornton .................. 435/32 | | 6,991,807 B2 | 1/2006 | Rudnic et al. ............. 424/468 |
| 6,440,462 B1 | 8/2002 | Raneburger et al. ....... 424/489 | | 7,008,633 B2 | 3/2006 | Yang et al. ............... 424/422 |
| 6,444,796 B1 | 9/2002 | Suh et al. ................. 536/7.2 | | 2001/0046984 A1 | 11/2001 | Rudnic .................. 514/210.09 |
| 6,468,864 B1 | 10/2002 | Sung et al. ............... 514/6 | | 2001/0048944 A1 | 12/2001 | Rudnic et al. ............. 424/468 |
| 6,479,496 B1 | 11/2002 | Wolff .................... 514/252.17 | | 2002/0004070 A1 | 1/2002 | Rudnic et al. ............. 424/468 |
| 6,495,157 B1 | 12/2002 | Pena et al. ................ 424/433 | | 2002/0004499 A1 | 1/2002 | Rudnic et al. ............. 514/192 |
| 6,497,901 B1 | 12/2002 | Royer ..................... 424/468 | | 2002/0015728 A1 | 2/2002 | Payumo et al. ............ 424/451 |
| 6,503,709 B1 | 1/2003 | Bekkaoui et al. .......... 435/6 | | 2002/0028920 A1 | 3/2002 | Lifshitz et al. ............. 536/7.1 |
| 6,506,886 B1 | 1/2003 | Lee et al. ................. 536/7.2 | | 2002/0042394 A1 | 4/2002 | Hogenkamp et al. ........ 514/53 |
| 6,514,518 B2 | 2/2003 | Monkhouse et al. ........ 424/427 | | 2002/0068078 A1 | 6/2002 | Rudnic et al. ............. 424/408 |
| 6,515,010 B1 | 2/2003 | Franchini et al. ........... 514/411 | | 2002/0068085 A1 | 6/2002 | Rudnic et al. ............. 424/468 |
| 6,515,116 B2 | 2/2003 | Suh et al. ................. 536/7.2 | | 2002/0081332 A1 | 6/2002 | Rampal et al. ............. 424/461 |
| 6,530,958 B1 | 3/2003 | Cima et al. ............... 623/23.51 | | 2002/0103261 A1 | 8/2002 | Ninkov ..................... 514/731 |
| 6,541,014 B2 | 4/2003 | Rudnic et al. ............. 424/400 | | 2002/0106412 A1 | 8/2002 | Rowe et al. ............... 424/490 |
| 6,544,555 B2 | 4/2003 | Rudnic et al. ............. 424/468 | | 2002/0115624 A1 | 8/2002 | Behar et al. ................ 514/42 |
| 6,548,084 B2 | 4/2003 | Rudnic et al. ............. 424/482 | | 2002/0119168 A1 | 8/2002 | Rudnic et al. ............. 424/400 |
| 6,550,955 B2 | 4/2003 | D'Silva .................... 366/130 | | 2002/0136764 A1 | 9/2002 | Rudnic et al. ............. 424/457 |
| 6,551,584 B2 | 4/2003 | Bandyopadhyay et al. .................. 424/78.04 | | 2002/0136765 A1 | 9/2002 | Rudnic et al. ............. 424/457 |
| | | | | 2002/0136766 A1 | 9/2002 | Rudnic et al. ............. 424/457 |
| 6,551,616 B1 | 4/2003 | Notario et al. ............ 424/464 | | 2002/0150619 A1 | 10/2002 | Rudnic et al. ............. 424/468 |
| 6,558,699 B2 | 5/2003 | Venkatesh ................ 424/464 | | 2002/0197314 A1 | 12/2002 | Rudnic et al. ............. 424/468 |
| 6,565,873 B1 | 5/2003 | Shefer et al. ............. 424/426 | | 2003/0012814 A1 | 1/2003 | Rudnic et al. ............. 424/468 |
| 6,565,882 B2 | 5/2003 | Rudnic .................... 424/472 | | 2003/0018295 A1 | 1/2003 | Henley et al. .............. 604/20 |
| 6,569,463 B2 | 5/2003 | Patel et al. ................ 424/497 | | 2003/0049311 A1 | 3/2003 | McAllister et al. ......... 424/452 |
| 6,585,997 B2 | 7/2003 | Moro et al. ............... 424/434 | | 2003/0064100 A1 | 4/2003 | Rudnic et al. ............. 424/468 |
| 6,599,884 B2 | 7/2003 | Avrutov et al. ............ 514/29 | | 2003/0073647 A1 | 4/2003 | Chao et al. ................ 514/42 |
| 6,605,069 B1 | 8/2003 | Albers et al. .............. 604/264 | | 2003/0073648 A1 | 4/2003 | Chao et al. ................ 514/42 |
| 6,605,300 B1 | 8/2003 | Burnside et al. ........... 424/452 | | 2003/0073826 A1 | 4/2003 | Chao et al. ................ 536/18.7 |
| 6,605,609 B2 | 8/2003 | Barbachyn et al. ........ 514/227.8 | | 2003/0077323 A1 | 4/2003 | Rudnic et al. ............. 424/468 |
| 6,605,751 B1 | 8/2003 | Gibbins et al. ............. 602/41 | | 2003/0086969 A1 | 5/2003 | Rudnic et al. ............. 424/468 |
| 6,610,323 B1 | 8/2003 | Lundberg et al. .......... 424/458 | | 2003/0091627 A1 | 5/2003 | Sharma .................... 424/465 |
| 6,610,328 B2 | 8/2003 | Rudnic et al. ............. 424/468 | | 2003/0096006 A1 | 5/2003 | Rudnic et al. ............. 424/468 |
| 6,617,436 B2 | 9/2003 | Avrutov et al. ............ 536/7.2 | | 2003/0096007 A1 | 5/2003 | Rudnic et al. ............. 424/468 |
| 6,623,757 B2 | 9/2003 | Rudnic et al. ............. 424/468 | | 2003/0096008 A1 | 5/2003 | Rudnic et al. ............. 424/468 |
| 6,623,758 B2 | 9/2003 | Rudnic et al. ............. 424/468 | | 2003/0099706 A1 | 5/2003 | Rudnic et al. ............. 424/468 |
| 6,624,292 B2 | 9/2003 | Lifshitz et al. ............. 536/7.2 | | 2003/0099707 A1 | 5/2003 | Rudnic et al. ............. 424/468 |
| 6,627,222 B2 | 9/2003 | Rudnic et al. ............. 424/468 | | 2003/0104054 A1 | 6/2003 | Rudnic et al. ............. 424/468 |
| 6,627,743 B1 | 9/2003 | Liu et al. .................. 536/7.2 | | 2003/0104055 A1 | 6/2003 | Rudnic et al. ............. 424/468 |
| 6,630,498 B2 | 10/2003 | Gudipati et al. ............ 514/397 | | 2003/0104056 A1 | 6/2003 | Rudnic et al. ............. 424/468 |
| 6,632,453 B2 | 10/2003 | Rudnic et al. ............. 424/468 | | 2003/0104058 A1 | 6/2003 | Rudnic et al. ............. 424/468 |
| 6,635,280 B2 | 10/2003 | Gudipati et al. ............ 424/469 | | 2003/0124196 A1 | 7/2003 | Weinbach et al. .......... 424/499 |
| 6,638,532 B2 | 10/2003 | Rudnic et al. ............. 424/468 | | 2003/0129236 A1 | 7/2003 | Heimlich et al. ............ 424/470 |
| 6,642,276 B2 | 11/2003 | Wadhwa .................. 514/781 | | 2003/0143268 A1 | 7/2003 | Pryce Lewis et al. ....... 424/464 |
| 6,663,890 B2 | 12/2003 | Rudnic et al. ............. 424/468 | | 2003/0147953 A1 | 8/2003 | Rudnic et al. ............. 424/468 |
| 6,663,891 B2 | 12/2003 | Rudnic et al. ............. 424/468 | | 2003/0190360 A1 | 10/2003 | Baichwal et al. ........... 424/470 |
| 6,667,042 B2 | 12/2003 | Rudnic et al. ............. 424/400 | | 2003/0198677 A1 | 10/2003 | Pryce Lewis et al. ....... 424/471 |
| 6,667,057 B2 | 12/2003 | Rudnic et al. ............. 424/468 | | 2003/0199808 A1 | 10/2003 | Henley et al. .............. 604/20 |
| 6,669,948 B2 | 12/2003 | Rudnic et al. ............. 424/400 | | 2003/0203023 A1 | 10/2003 | Rudnic et al. ............. 424/468 |
| 6,669,955 B2 | 12/2003 | Chungi et al. ............. 424/464 | | 2003/0206951 A1 | 11/2003 | Rudnic et al. ............. 424/468 |
| 6,673,369 B2 | 1/2004 | Rampal et al. ............. 424/468 | | 2003/0216555 A1 | 11/2003 | Lifshitz et al. ............. 536/7.1 |
| 6,682,759 B2 | 1/2004 | Lim et al. .................. 424/468 | | 2003/0216556 A1 | 11/2003 | Avrutov et al. ............ 536/7.2 |
| 6,696,426 B2 | 2/2004 | Singh et al. ............... 514/58 | | 2003/0232089 A1 | 12/2003 | Singh et al. ............... 424/488 |
| 6,702,803 B2 | 3/2004 | Kupperblatt et al. ....... 604/890.1 | | 2003/0235615 A1 | 12/2003 | Rudnic ...................... 424/468 |
| 6,706,273 B1 | 3/2004 | Roessler ................... 424/422 | | 2004/0018234 A1 | 1/2004 | Rudnic et al. ............. 424/468 |
| 6,723,340 B2 | 4/2004 | Gusler et al. .............. 424/468 | | 2004/0033262 A1 | 2/2004 | Kshirsagar et al. ......... 424/468 |
| 6,723,341 B2 | 4/2004 | Rudnic et al. ............. 424/468 | | 2004/0043073 A1 | 3/2004 | Chen et al. ................ 424/486 |
| 6,730,320 B2 | 5/2004 | Rudnic et al. ............. 424/468 | | 2004/0047906 A1 | 3/2004 | Percel et al. ............... 424/468 |
| 6,730,325 B2 | 5/2004 | Devane et al. ............. 424/489 | | 2004/0048814 A1 | 3/2004 | Vanderbist et al. .......... 514/29 |
| 6,735,470 B2 | 5/2004 | Henley et al. .............. 604/20 | | 2004/0052842 A1 | 3/2004 | Rudnic et al. ............. 424/468 |
| 6,740,664 B2 | 5/2004 | Cagle et al. ............... 514/311 | | 2004/0058879 A1 | 3/2004 | Avrutov et al. ............ 514/29 |
| 6,746,692 B2 | 6/2004 | Conley et al. .............. 424/468 | | 2004/0091528 A1 | 5/2004 | Rogers et al. .............. 424/468 |
| 6,756,057 B2 | 6/2004 | Storm et al. ............... 424/472 | | 2004/0126427 A1 | 7/2004 | Venkatesh et al. .......... 424/468 |

| | | | |
|---|---|---|---|
| 2004/0176737 A1 | 9/2004 | Henley et al. | 604/501 |
| 2004/0219223 A1 | 11/2004 | Kunz | 424/489 |
| 2004/0253249 A1 | 12/2004 | Rudnic et al. | 424/184.1 |
| 2004/0265379 A1 | 12/2004 | Conley et al. | 424/465 |
| 2005/0053658 A1 | 3/2005 | Venkatesh et al. | 424/468 |
| 2005/0064033 A1 | 3/2005 | Notario et al. | 424/468 |
| 2005/0064034 A1 | 3/2005 | Li et al. | 424/469 |
| 2005/0163857 A1 | 7/2005 | Rampal et al. | 424/489 |
| 2005/0203076 A1 | 9/2005 | Li et al. | 514/183 |
| 2005/0203085 A1 | 9/2005 | Li et al. | 514/224.5 |
| 2005/0209210 A1 | 9/2005 | Ding et al. | 514/183 |
| 2005/0238714 A1 | 10/2005 | Rudnic et al. | 424/468 |
| 2005/0256096 A1 | 11/2005 | Combrink et al. | 514/183 |
| 2005/0261262 A1 | 11/2005 | Ma et al. | 514/183 |
| 2005/0277633 A1 | 12/2005 | Ma et al. | 514/224.5 |
| 2006/0019985 A1 | 1/2006 | Ma et al. | 514/306 |
| 2006/0019986 A1 | 1/2006 | Ding et al. | 514/306 |
| 2006/0111302 A1 | 5/2006 | Romesberg et al. | 514/18 |

FOREIGN PATENT DOCUMENTS

| | | |
|---|---|---|
| EP | 0293885 | 12/1988 |
| EP | 0436370 | 7/1991 |
| EP | 0652008 | 5/1995 |
| FR | 2585948 | 2/1982 |
| GB | 2087235 | 5/1982 |
| WO | WO 90/08537 | 8/1990 |
| WO | WO 94/27557 | 12/1994 |
| WO | WO 95/20946 | 8/1995 |
| WO | WO 95/30422 | 11/1995 |
| WO | WO 96/04908 | 2/1996 |
| WO | WO 97/22335 | 6/1997 |
| WO | WO 97/43277 | 11/1997 |
| WO | WO 98/22091 | 5/1998 |
| WO | WO 98/46239 | 10/1998 |
| WO | WO 99/03453 | 1/1999 |
| WO | WO 99/40097 | 8/1999 |
| WO | WO 00/48607 | 8/2000 |
| WO | WO 00/61116 | 10/2000 |
| WO | WO 01/26663 | 4/2001 |
| WO | WO 02/38577 | 5/2002 |
| WO | WO 03/029439 | 4/2003 |
| WO | WO 05/056754 | 6/2005 |
| WO | WO 05/070941 | 8/2005 |

OTHER PUBLICATIONS

Borman, Chemistry Highlights 2005, Chemical & Engineering News, Dec. 19, 2005, vol. 83, No. 51, pp. 15-20.
Bradley, Staphylococcus Aureus Pneumonia: Emergence of MRSA in the Community, Semin Respir Crit Care Med. 2005; 26 (6): 643-649.
Cirz et al., Inhibition of Mutation and Combating the Evolution of Antibiotic Resistance, PLOS Biology, Jun. 2005, vol. 3, Issue 6,e176, pp. 1024-1033.
Darst, New Inhibitors Targeting Bacterial RNA Polymerase, TRENDS in Biochemical Sciences, vol. 29, No. 4, Apr. 2004, pp. 159-162.
Dellit, M.D., Tim, University of Washington and Infectiouse Diseases Society of Washington; Jeffrey Duchin, MD, Public Health-Seattle & King County and University of Washington; Jo Hofmann, MD, Washington State Department of Health and University of Washing; Erika Gurmai Olson, MD, Tacoma-Pierce County Health Department Antibiotic Resistance Task Force, Interim Guidelines for Evaluation and Management of Community-Associated Methicillin-Resistant Staphylococcus Aureus Skin and Soft Tissue Infections in Outpatient Settings, Sep. 2, 2004.
Geiger et al., Metabolites of Microorganisms. 247, Phenazines from Streptomyces Antibioticus, Strain Tu 2706, J Antibiot (Tokyo). Nov. 1988;41 (11): 1542-51.
Gorwitz et al., Strategies for Clinical Management of MRSA in the Community: Summary of an Experts' Meeting Convened by the Centers for Disease Control and Prevention, Department of Health and Human Services Centers for Disease Control and Prevention, Mar. 2006.
Henry, Disabling Resistance Inhibiting Key Protease Prevents Bacteria From Evolving Drug Resistance, Chemical and Engineering News, May 16, 2005, vol. 83, No. 20, p. 8.
Johnson, N.J. Experts Urge Prudent Antibiotic Use, Examiner.Com, The Associated Press, Jul. 31, 2006.
Kitahara et al., Saphenamycin, A Novel Antibiotic From A Strain of Steptomyces, J Antibiot (Tokyo). Oct. 1982; 35(10):1412-4.
Laursen et al., Solid-Phase Synthesis of New Saphenamycin Analogues with Antimicrobial Activity, Bioorg. Med. Chem. Lett. Jan. 21, 2002; 12(2):171-5.
Laursen et al., First Synthesis of Racemic Saphenamycin and its Enantiomers. Investigation of Biological Activity, Bioorg. Med. Chem. Mar. 6, 2003;11(5):723-31.
Laursen et al., Efficient Synthesis of Glycosylated Phenazine Natural Products and Analogs with DISAL (Methyl 3, 5-Dinitrosalicylate) Glycosyl Donors, Org. Biomol. Chem. Sep. 21, 2003; 1(18):3147-53.
Reusser, Inhibition of Ribosomal and RNA Polymerase Functions by Rubradirin and Its Aglycone, J Antibiot (Tokyo). Nov. 1979;32(11):1186-92.
Rihn, et al., Community-Acquired Methicillin-Resistant Staphylococcus Aureus: An Emerging Problem in the Athletic Population, AM J Sports Med. Dec. 2005;33(12): 1924-9.
Salmenlinna et al., Community-Acquired Methicillin-Resistant Staphylococcus Aureus, Finland, Emerg. Infect. Dis. Jun. 2002; 8(6):602-7.
Salmenlinna et al., Community-Acquired Methicillin-Resistant Staphylococcus Aures, Finland, Emerging Infectious Diseases, vol. 8, No. 6, Jun. 2002, pp. 602-607.
Vandenesch et al., Community-Acquired Methicillin-Resistant Staphylococcus Aureus Carrying Panton-Valentine Leukocidin Genes: Worldwide Emergence, Emerg. Infect. Dis. Aug. 2003;9(8):978-84.
Can We Prevent Bacteria From Developing Resistant to Antibiotics?, Sep. 2005, AAPS News Magazine 15.
Healthcare-Associated Methicillin Resistant Staphylococcus Aureus (HA-MRSA), Department of Health and Human Services, Centers for Disease Control and Prevention, Jun. 1, 2005.
Methicillin-Resistant Staphylococcus Aureus, HealthLink, Medical College of Wisconsin, Information Provided by the Wisconsin Department of Health and Family Services, Article Reviewed: Apr. 10, 2000 Medical College of Wisconsin.
Methicillin-Resistant Staphylococcus Aureus (MRSA) Infection, Written by Dr. Alan Johnson, Clinical Scientst, Website: www.mrsasupport.co.uk, Jan. 8, 2005.
The Public's Health, Back-To-School: Review Immunization Records Early, What Doctors and Parents Need to Know About Immunizations and School, vol. 5, No. 7, Jul.-Aug. 2005.
Sulfonamide Class Antibiotics, ChemicalLand21.com.
Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).
Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.
Berry et al., Bacteriological Efficacies of Three Macrolides Compared with Those Amoxicillin-Clavulanate Against Streptococcus Pneumoniae and Haemophilus Influenzae, Antimicrob Agents Chemother. Dec. 1998; 42(12: 3193-3199.
Bhargava et al., Pulsed Feedings During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.
Bhargava et al., Pulsed Feeding During Fed-Batch Aspergillus Oryzae Fermentation Leads to Improved Oxygen Mass Transfer, Biotechnol. Prog. 2003, 19, 1091-1094.
Bhargava et al., Pulsed Addition of Limiting-Carbon During Aspergillus Oryzae Fermentation Leads to Improved Productivity of a Recombinant Enzyme, Biotechnology and Bioengineering, vol. 82, No. 1, Apr. 5, 2003, pp. 111-117.

Bishai, Comparative Effectiveness of Different Macrolides: Clarithromycin, Azithromycin, and Erythromycin, Johns Hopkins Point of Care Information Technology (POC-IT).

Bradley, Staphylococcus Aureus Pneumonia: Emergence of MRSA in the Community, Semin Respir Crit Care Med. 2005; 26 (6): 643-649.

Brogden et al., Cefixime. A Review of Its Antibacterial Activity. Pharmacokinetic Properties and Therapeutic Potential, Drugs, Oct. 1989; 38 (4): 524-50. (Abstract).

Burgess et al., A Time-Kill Evaluation of Clarithromycin and Azithromycin Against Two Extracellular Pathogens and the Development of Resistance, The Annals of PharmacotherapyL vol. 33, No. 12, pp. 1262-1265. (Abstract).

Byfield et al., Relevance of the Pharmacology of Oral Tegafur to its Use as a 5-FU Pro-Drug., Cancer Treat Rep. Jun. 1985; 69 (6): 645-52. (Abstract).

Cappelletty et al., Bactericidal Activities of Cefprozil, Penicillin, Cefaclor, Cefixime, and Loracarbef against Penicillin-Susceptible and —Resistant Streptococcus Pneumoniae in an In Vitro Pharmacodynamic Infection Model, Antimicrobial Agents and Chemotherapy, May 1996,p/ 1148-1152.

Cha et al., Pulsatile Delivery of Amoxicillin Against Streptococcus Pneumoniae, Journal of Antimicrobial Chemotherapy, Advance Access Published Oct. 14, 2004.

Craig, Antibiotic Selection Factors and Description of a Hospital-Based Outpatient Antibiotic Therapy Program in the USA, Eur J Clin Microbiol Infect Dis. Jul. 1995; 14(7):636-42. (Abstract).

Cremieux et al., Ceftriaxone Diffusion into Cardiac Fibrin Vegetation. Qualitative and Quantitative Evaluation by Autoradiography, Fundam Clin Pharmacol. 1991;5(1):53-60. (Abstract).

Endo et al., Fungicidal Action of Aureobasidin A, a Cyclic Depsipeptide Antifungal Antibiotic, against Saccharomyces Cerevisiae, Antimicrobial Agents and Chemotherapy, Mar. 1997, p. 672-676.

Erah et al., The Stability of Amoxicilin, Clarithromycin and Metronidazole in Gastric Juice: Relevance to the Treatment of Helicobacter Pylori Infection, J Antimicrob Chemother Jan. 1997;39 (1):5-12. (Abstract).

Fang, A Study of the Ethical Considerations and Implications, Prozac Weekly and Sarafem in the Wake of Prozac □ $ Patent Expiration, 5.22J/10.02J, Biotechnology and Engineering.

Feder et al., Once-Daily Therapy for Streptococcal Pharyngitis With Amoxicillin, American Academy of Pediatrics, vol. 103(1), Jan. 1999, pp. 47-51.

Freeman et al., The Cyclosporin-Erthromycin Interaction: Impaired First Pass Metabolism in the Pig, Br J Pharamcol. Jul. 1991;103(3):1709-12. (Abstract).

Frimodt-Moller, Correlation Between Pharmacokinetic / Pharmacodyamic Parameters and Efficacy for Antibiotics in the Treatment of Urinary Tract Infection, Int J. Antimicrob. Agents, 19 (2002) 546-53.

Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2003) 51, 101-106.

Gill et al., In Vivo Activity and Pharmacokinetic Evaluation of a Novel Long-Acting Carbapenem Antibitoic, MK-826 (L-749, 345), Antimicrobial Agents and Chemotherapy, Aug. 1998;42(8):1996-2001.

Gnarpe et al., Penicillin Combinations Against Multi-Resistant Urinary Pathogens as an Alternative to Gentamycin Treatment, Microbios 1976;16(65-66):201-6. (Abstract).

Gordon et al., Rationale for Single and High Dose Treatment Regimens with Azithromycin, Pediatric Infectious Disease Journal. 23(2) Supplement: S102-S107, Feb. 2004. (Abstract).

Goswick et al., Activities of Azithromycin and Amphotericin B Against Naegleria Fowleri In Vitro and in a Mouse Model of Primary Amebic Meningoencephalitis, Antimicrob Agents Chemother. Feb. 2003; 47(2): 524-528.

Harbarth et al., Prolonged Antibiotic Prophylaxis After Cardiovascular Surgery and Its Effect on Surgical Site Infections and Antimicrobial Resistance, Circulation Jun. 27, 2000; 101:2916-2921.

Haney, New Drugs Kill Bacteria Resistant to Antibiotics, Called Ketolides, They are Chemically New to the Harmful Bugs, Thursday, Sep. 21, 2000, Seattle Post-Intelligencer.

Harris et al., Esophageal Carcinoma: Curative Treatment, Combined Modalities, The Virtual Hospital.

Hickey et al., Production of Enterolysin A by a Raw Milk Enterococcal Isolate Exhibiting Multiple Virulence Factors, Microbiology 149 (2003), 655-664.

Hirata et al., Pharmacokinetic Study of S-1, a Novel Oral Fluorouracil Antitumor Drug, Clinical Cancer Research vol. 5, 2000-2005, Aug. 1999.

Hoff et al., Phase I Study with Pharmacokinetics of S-1 on an Oral Daily Schedule for 28 Days in Patients with Solid Tumors, Clinical Cancer Research vol. 9, 134-142, Jan. 2003.

Hoffman et al., Pharamcodynamic and Pharmacokinetic Rationales for the Development of an Oral Controlled-Release Amoxicillin Dosage Form, Journal of Controlled Release 54 (1998) 29-37.

Hoffman et al., Influence of Macrolide Susceptibility on Efficacies of Clarithomycin and Azithromycin Against Streptococcus Pneumoniae in a Murine Lung Infection Model, Antimicrobial Agents and Chemotherapy, Feb. 2003, p. 739-746, vol. 47, No. 2.

Hyde et al., Macrolide Resistance Among Invasive Steptococcus Pneumoniae Isolates, JAMA. Oct. 17, 2001; 286(15):1857-62. (Abstract).

Iba et al., Comparison Between Continuous Intravenous and Oral Administration of 5-FU with LV, Gan To Kagaku Ryoho. Apr. 1999; 26(5): 631-5 (Abstract).

Jacobs, Pharmacodynamic Approach to Antimicrobial Treatment for Respiratory Infections, Department of Pathology, Case Western Reserve University.

Kaplan et al., Macrolide Therapy of Group A Steptococcal Pharyngitis: 10 Days of Macrolide Therapy (Clarithomycin) is More Effective in Streptococcal Eradication Than 5 Days (Azithromycin), Clin Infect Dis. Jun. 15, 2001;32(12):1798-802. Epub May 21, 2001. (Abstract).

Klugman, Bacteriological Evidence of Antibiotic Failure in PneumococcalLower Respiratory Tract Infections, Eur Respir J 2002; 20 Suppl. 36, 3s-8s.

Kramar et al., Statistical Optimisation of Diclofenac Sustained Release Pellets Coated with Polymethacrylic Films, Int J Pharm. Apr. 30, 2003;256(1-2):43-52. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, Oct. 2000. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, 2000.

Lamb et al., Ceftriaxone: An Update of its Use in the Management of Community-Acquired and Noscocomial Infections, Drugs. 2002;62(7):1041-89. (Abstract).

Lemer-Tung et al., Pharmacokinetics of Intrapericardial Administration of 5-Fluorouracil, Cancer Chemother Pharmacol. 1997;40(4):318-20. (Abstract).

Lin et al., Multiple-Dose Pharmacokinetics of Ceftibuten in Healthy Volunteers, Antimicrobial Agents and Chemotherapy, Feb. 1995, p. 356-358.

Lindsey et al., Extraction of Antibiotics From Agricultural Wastewater, USGS, 220th ACS Meeting Washington, D.C.; Aug. 20-24, 2000 (Abstract).

Livermore et al., Activity of Ertapenem Against Neisseria Gonorrhoeae, Journal of Antimicrobial Chemotherapy 2004 54(1):280-281.

Lovmar et al., Kinetics of Macrolide Action, The Josamycin and Erthromycin Cases, J. Biol. Chem., vol. 279, Issue 51, 53506-53515, Dec. 17, 2004.

Mainz et al., Pharmacokinetics of Lansoprazole, Amoxicillin and Clarithromycin After Simultaneous and Single Administration, Journal of Antimicrobial Chemotherapy (2002) 50, 699-706.

Marten et al., Monthly Report, Jul. 2004, Pulsatile Dosing of Antifungal Compounds, UMBC; to Dr. Robert J. Guttendorf, Advancis Pharmaceutical Corp.

Marten et al., Monthly Report, Aug. 2004, Pulsatile Dosing of Antifungal Compounds, UMBC; to Dr. Robert J. Guttendorf, Advancis Pharmaceutical Corp.

Mazzei et al., How Macrolide Pharmacodynamics Affect Bacterial Killing, Infect Med 16(sE):22-28, 1999.(Abstract).

Nightingale, Pharmacokinetics and Pharmacodynamics of Newer Macrolides, Pediatric Infectious Disease Journal. 16(4):438-443, Apr. 1997. (Abstract).

Olofinlade et al. Anal Carcinoma: A 15-Year Retrospective Analysis, Scand J Gastroenterol 2000:35;1194-1199.

Pacifico et al., Comparative Efficacy and Safety of 3-Day Azithromycin and 10-Day Penicillin V Treatment of Group A Beta-Hemolytic Streptococcal Pharyngitis in Children, Antimicroial Agents and Chemotherapy, 04 1996, 1005-1008, vol. 40, No. 4. (Abstract).

Parmar-Lapasia et al., A Comparison of Two Macrolide Antibiotics in the Treatment of Community-Acquired Infections P & T (Pharmacy & Therapeutics), Oct. 2003, vol. 28, No. 10.

Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 (Nov. 15) 2001: 4267-4269.

Polak, Pharmacokinetics of Amphotericin B and Flucytosine, Postgrad Med J. Sep. 1979;55(647):667-70. (Abstract).

Porter et al., Antibiotics and Infectious Diseases in Otaryngology—HNS, Grand Rounds Presentation, UTMB, Dept. of Otolaryngology, May 8, 2002.

Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extracasation Injury Associated with the Use of Vesicant Antineoplastic Agents, Baylor College of Medicine, Aug. 6, 1998.

Ranga Rao et al., Influence of Molecular Size and Water Solubility of the Solute on its Release from Swelling and Erosion Controlled Polymeric Matrices, Journal of Controlled Release, 12 (1990) 133-141.

Reza et al., Comparative Evaluation of Plastic, Hydrophobic and Hydrophilic Polymers as Matrices for Controlled-Release Drug Delivery, J. Pharm Pharmaceut Sci, 6(2):282-291, 2003.

Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Miligram Single Oral Dose and Rate of Eradication of Infection in Vaginal Candidasis, Antimicrob Agents Chemother. May 1990; 34(5):909-10 (Abstract).

Rivkees et al., Dexamethasone Treatment of Virilizing Cogenital Adrenal Hyperplasia: The Ability to Achieve Normal Growth, Pediatrics 2000; 106; 767-773.

Roblin et al., In Vitro Activity of a New Ketolide Antibiotic, HMR 3647, Against Chlamydia Pneumoniae, Antimicrob Agents Chemother. Jun. 1998; 42(6): 1515-1516.

Santini et al., The Potential of Amifostine: From Cytoprotectant to Therapeutic Agent, Haematologica Nov. 1999; 84(ii): 1035-1042.

Sanz et al., Cefepime Plus Amikacin Versus Piperacillin-Tazobactam Plus Amikacin for Initial Antibiotic Therapy in Hematology Patients with Febrile Neutropenia: Results of an Open, Randomized Multicentre Trial, Journal of Antimicrobial Chemotherapy (2002) 50, 79-88.

Schaad et al., Azithromycin Versus Penicillin V for Treatment of Acute Group A Streptococcal Pharyngitis, The Pediatric Infectious Disease Journal: vol. 21(4) Apr. 2002 pp. 304-308.

Schweizer et al., "Single Shot" Prevention in Abdominal Surgery. Antibiotics with Long Half-Life (Cefriazone Omidazole) vs. Antibiotics with Short Half-Life (Cefazolin, Metronidazole, Clindamycin), Helv Chir Acta. Apr. 1994; 60(4):483-8. (Abstract).

Shvartzman et al., Treatment of Streptococcal Pharyngitis with Amoxycillin Once A Day, BMJ vol. 306, pp. 1170-1172, May 1, 1993.

Stringer et al., Section 3: Diseases of the Ear, Part 4: Inner Ear, Chapter 46: Ototoxicity, Paparella: vol. II, Otology and Neuro-Otology.

Suda et al., The Synthesis and In Vitro and In Viv Stability of 5-Fluorouracil Prodrugs Which Possess Serum Albumin binding Potency, Biol Pharm Bull. Sep. 1993;16(9):876-8 (Abstract).

Sandip et al., Controlled Release Formulation of Tramadol Hydrochloride Using Hydrophillic and Hydrophobic Matrix System, AAPS PharmSciTech 2003; 4 (3) Article 31.

Todar's Online Textbook of Bacteriology, Antimicrobial Agents Used in Treatment of Infectious Disease, 2002 Kenneth Todar University of Wisconsin-Madison Department of Bacteriology.

Vanderkooi et al., Antimicrobial Resistance and the Pneumococcus, Infectious Diseases and Microbiology, vol. 3, Issue 5, May 2004.

Villalobos et al., Pharmacokinetics and Pharmacodynamics of Antibacterial Agents in Pediatrics: A Practical Approach, Jacksonville Medicine, Aug. 1998.

Waters, Colorectal Cancer-Drug Treatment, Hospital Pharmacist, vol. 11, pp. 179-192, May 2004.

Wattenberg, Prevention of Carcinogenesis of the Respiratory Tract By Chemoprecentive Agents Delivered By Aerosol, International Society of Cancer Chemoprevention. vol. 1, No. 5, Jan. 2003.

Whitehead et al., Amoxycilin Release From a Floating Dosage Form Based on Alginates, International Journal of Pharmaceutics 210 (2000) 45-49.

Yousef et al., Combined Action of Amoxycillin and Dicloxacillin Against Staphylococcus Aureus In Vitro. Pharmazle Sep. 1985; 40(9):650-1. (Abstract).

About Macrolides, About That Bug.com.

Acepromazine Maleate, DRUGS.

Allergy Site Navigator, Drug Classification A-D.

Amoxycillin (As Trihydrate), Moxyvit.

Amoxicillin + Clavulanate, PetPlace.com.

Answers.com, Macrolide.

Antimetabolites, GPnotebook.

Augmentin, Product Information, GlaxoSmithKline, Physicans Desk References, pp. 1421-1433.

Augmentin XR (PDR entry for) (GlaxoSmithKline), (Amoxicillin/Clavulanate Potassium), Extended Release Tablets, Jun. 2004.

Beta Lactam Antibiotics, Health 24.com.

Biaxin XL, Once-Daily Blaxin XL Clarithromycin Extended-Release Tablets, Abbott Laboratories Online.

Biaxin XL, Once-daily, Abbott.

Biaxin, Dosage and Administration.

Biaxin Filmtab, Biaxin XL Filmtab, Biaxin Granules, pp. 1-25, Abbott Laboratories.

Body Chemistry, Acid Alkaline Foods, Acid Reflux? Gas, Acid Indigestion, Acid/Alkaline Balance.

Carers of Crohns, Antibiotics.

Citizen Petition, McNeils Consumer & Specialty Pharmaceuticals, Mar. 19, 2004.

Clarithromycin Extended-Release Scientific Posters Presented to the 39th Interscience Conference on Antimicrobial Agents and Chemotherapy (ICAAC), San Francisco, Sep. 26-29, 1999.

Clearance and the Elimination Rate Constant, Ke (Elimination Rate)—Half-Life, Oct. 14, 2002.

Complementary Medicine Saves Money, Medicine, Greenhealthwatch.com.

Criss-Reference Art Collections, 901-907; USPTO.gov.

Declaration of Michael J. Rybak. fromthe prosecution history of U.S. Appl. No. 09/792,092; Sep. 23, 2002.

Dispensing Errors With Depakote, New Formulation Creates Confusion, Patient Safety, Practioners Reporting News, USP Issued Mar. 3, 2001.

Drugs.com, Drug Information For Diclofenac (Topical).

Drug, Bio-Affecting and Body Treating Compositions (Class 424), 475 Sustained or differential release, United States Patent and Trademark Office.

Elimination Rate Constant/Half-Life, Ke (Elimination Rate)—Half-Life, Oct. 14, 2002.

Emulsions.

Encyclopedia Britannica Online, Types of Drugs >Antimicrobial Drugs>Antibiotics>Macrolides.

Excenel, Swine Health Management, Prewean Program. Pfizer Salud Animal.

Fabrication of Metronidazole Strips, 996 Die Pharmazie 50(1995) Feb. No. 2.

Five vs. 10 Days of Therapy for Streptococcal Pharyngitis, American Family Physician, Feb. 15, 2001.

Food and Drug Administration Center for Drug Evaluation and Research Approved Drug Products With Therapetutic Equivalence Evaulations, 24th Edition.

Getting a Drug Into the Body: Absorption.

Highlights on Antineoplastic Drugs, Pharmacia, vol. 11, No. 4, 1993.

Jock Itch and Other dermatophytes . . . , Mycolog.

Klaritran, Ranaxy(SA)(PTY) LTD, Jun. 2005.

Klucel Hydroxypropylcellulose (HPC). Hercules Incorporated.

MedicineNet.com, Generic Name: Acyclovir, Brand Name: Zovirax, Dec. 31, 1997.

Meeting the Challenge of a New Generator of Respiratory Pathogens, MAC.

The Merck Index, An Encyclopedia of Chemicals, Drugs, an Biologicals, Twelfth Edition, pp. 397-398.

Methods of Formulating Controlled Release Products Outside of the Claims of Forest Laboratory Patents U.S. 4,369,172 and U.S. 4,389,393, Technical Information, Dow Chemical, Feb. 1991.

Miconazole, The Merck Index Results-Form View, Monograph No. 06202.

Mode of Action of Macrolides in Blocking Translation During Bacterial Protein Synthesis: Blocking Peptidyltransferase. Doc Kaiser's Microbiology Home Page, Oct. 13, 2004.

Module 8—Therapeutics May 25, 2002, Newcastle., BPAIIG Immunology/Infectious Diseases Training Programme, Module: Therapeutics.

Monistat, Which Treatment Is Right for You?, Vaginal vs. Oral Therapy.

Neisseria Meningitidis, The Doctor's Doctor, Nov. 8, 2004.

New-Generation Aromatase Inhibitor for Breast Cancer: Anastrozole Challenges Tamoxifen in First-Line Therapy, 10th European Cancer Conference (ECCO 10), Vienna, Austria /Sep. 12-16, 1999.

New Product Newswire, Drug Topics Archive, Aug. 5, 2002.

Nitrofurantoin, Eckered Prescription Advisor, Feb. 15, 2001.

Nursing, Cancer Nursing: Principles and Practice, Fifth Edition, Jones and Bartlett Publishers, 2000.

Oral Capecitabine Should Improve Convenience of Chemoradiation for Locally Advanced Rectal Cancer-New Treatment Appears to be Safe and Effective, PeerView Press, Chemotherapy (ICAAC), Sep. 27-30, 2002; San Diego, CA., 40th Annual Meeting of Infectious Diseases Society.

Oral Extended (Controlled) Release Dosage Forms, In Vivo Bioequivalence and In Vitro Dissolution Testing, Office of Generic Drugs.

Pharmaceuticals, Pharmacos Unit F2 Pharmaceuticals V 6.0, Eudralex Collection 3AQ19a 1992.

Physicians Desk Reference, PDR 57 Edition 2003, p. 402/Abbott.

Principles of Diagnosis of Infectious Diseases and Antimicrobial Therapy, Chapter 1.

Procardia XL (Nifedpine) Extended Release Tablets For Oral Use, 69-4467-00-8, Pfizer Labs, Aug. 2003.

Summary of Product Characteristics, Doxycycline Capsules BP 50mg.

Sustained or Differential Release Type, USPTO Classification Definitions (Dec. 2002 Edition) 964.

Sustained-Release Dosage Forms, Degussa, Rohm Pharma Polymers.

Testicular Cancer: Questions and Answers, Cancer Facts, National Cancer Institute, Aug. 14, 2003.

Traditional Chemotherapy, Chapter 25 from Prevention and Therapy of Cancer and Other Common Disease: Alternative and Traditional Approaches; Infromedix 1996.

* cited by examiner

ANTIVIRAL PRODUCT, USE AND FORMULATION THEREOF

This application is a continuation of U.S. application Ser. No. 10/288,000, filed Nov. 5, 2002 now U.S. Pat. No. 6,984,401, which is a continuation of U.S. application Ser. No. 09/791,906, filed Feb. 22, 2001 now U.S. Pat. No. 6,541,014, which is a continuation-in-part of U.S. application Ser. No. 09/687,237, filed on Oct. 13, 2000 now abandoned, the disclosures of each of which are hereby incorporated by reference in their entireties.

This invention relates to an antiviral product, as well as the use and formulation thereof.

A wide variety of antivirals have been used, and will be used, in order to combat viral infection. In general, such antivirals can be administered by a repeated dosing of immediate release dosage forms, which results in poor compliance or as a controlled release formulation (slow release) at higher administered doses. The present invention is directed to providing for an improved antiviral product.

In accordance with one aspect of the present invention, there is provided an antiviral pharmaceutical product which is comprised of at least two, preferably at least three, antiviral dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the antiviral contained therein at different times after administration of the antiviral product.

Thus, in accordance with an aspect of the present invention, there is provided a single or unitary antiviral product that has contained therein at least two, preferably at least three antiviral dosage forms, each of which has a different release profile, whereby the antiviral contained in each of such dosage forms is released at different times.

In accordance with a further aspect of the invention, the antiviral product may be comprised of at least four different dosage forms, each of which starts to release the antiviral contained therein at different times after administration of the antiviral product.

The antiviral product generally does not include more than five dosage forms with different release times.

In accordance with a preferred embodiment, the antiviral product has an overall release profile such that when administered the maximum serum concentration of the total antiviral released from the product is reached in less than twelve hours, preferably in less than eleven hours. In an embodiment, the maximum serum concentration of the total antiviral released from the antiviral product is achieved no earlier than four hours after administration.

In accordance with one preferred embodiment of the invention, there are at least three dosage forms. One of the at least three dosage forms is an immediate release dosage form whereby initiation of release of the antiviral therefrom is not substantially delayed after administration of the antiviral product. The second and third of the at least three dosage forms is a delayed dosage form (which may be a pH sensitive or a non-pH sensitive delayed dosage form, depending on the type of antiviral product), whereby the antiviral released therefrom is delayed until after initiation of release of the antiviral from the immediate release dosage form. More particularly, the antiviral release from the second of the at least two dosage forms achieves a $C_{max}$ (maximum serum concentration in the serum) at a time after the antiviral released from the first of the at least three dosage forms achieves a $C_{max}$ in the serum, and the antiviral released from the third dosage form achieves a $C_{max}$ in the serum after the $C_{max}$ of antiviral released from the second dosage form.

In one embodiment, the second of the at least two dosage forms initiates release of the antiviral contained therein at least one hour after the first dosage form, with the initiation of the release therefrom generally occurring no more than six hours after initiation of release of antiviral from the first dosage form of the at least three dosage forms.

In general, the immediate release dosage form produces a $C_{max}$ for the antiviral released therefrom within from about 0.5 to about 2 hours, with the second dosage form of the at least three dosage forms producing a $C_{max}$ for the antiviral released therefrom in no more than about four hours. In general, the $C_{max}$ for such second dosage form is achieved no earlier than two hours after administration of the antiviral product; however, it is possible within the scope of the invention to achieve $C_{max}$ in a shorter period of time.

As hereinabove indicated, the antiviral product may contain at least three or at least four or more different dosage forms. For example, if the antiviral product includes a third dosage form, the antiviral released therefrom reaches a $C_{max}$ at a time later than the $C_{max}$ is achieved for the antiviral released from each of the first and second dosage forms. In a preferred embodiment, release of antiviral from the third dosage form is started after initiation of release of antiviral from both the first dosage form and the second dosage form. In one embodiment, $C_{max}$ for antiviral release from the third dosage form is achieved within eight hours.

In another embodiment, the antiviral product contains at least four dosage forms, with each of the at least four dosage forms having different release profiles, whereby the antiviral release from each of the at least four different dosage forms achieves a $C_{max}$ at a different time.

As hereinabove indicated, in a preferred embodiment, irrespective of whether the antiviral contains at least two or at least three or at least four different dosage forms each with a different release profile, $C_{max}$ for all the antiviral released from the antiviral product is achieved in less than twelve hours, and more generally is achieved in less than eleven hours.

In a preferred embodiment, the antiviral product is a once a day product, whereby after administration of the antiviral product, no further product is administered during the day; i.e., the preferred regimen is that the product is administered only once over a twenty-four hour period. Thus, in accordance with the present invention, there is a single administration of an antiviral product with the antiviral being released in a manner such that overall antiviral release is effected with different release profiles in a manner such that the overall $C_{max}$ for the antiviral product is reached in less than twelve hours. The term single administration means that the total antiviral administered over a twenty-four hour period is administered at the same time, which can be a single tablet or capsule or two or more thereof, provided that they are administered at essentially the same time.

Applicant has found that a single dosage antiviral product comprised of at least three antiviral dosage forms each having a different release profile is an improvement over a single dosage antiviral product comprised of an antiviral dosage form having a single, release profile. Each of the dosage forms of antiviral in a pharmaceutically acceptable carrier may have one or more antivirals and each of the dosage forms may have the same antiviral or different antivirals.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antiviral may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antiviral release from such fourth dosage form may be initiated prior to or after release from the second or third dosage form.

The antiviral product of the present invention, as hereinabove described, may be formulated for administration by a variety of routes of administration. For example, the antiviral product may be formulated in a way that is suitable for topical administration; administration in the eye or the ear; rectal or vaginal administration; as nose drops; by inhalation; as an injectable; or for oral administration. In a preferred embodiment, the antiviral product is formulated in a manner such that it is suitable for oral administration.

For example, in formulating the antiviral product for topical administration, such as by application to the skin, the at least two different dosage forms, each of which contains an antiviral, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an antiviral product in the form of a patch, which includes antiviral dosage forms having different release profiles, as hereinabove described.

In addition, the antiviral product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antiviral product with at least three different dosage forms with different release profiles may be formulated for rectal or vaginal administration, as known in the art. This may take the form of a cream or emulsion, or other dissolvable dosage form similar to those used for topical administration.

As a further embodiment, the antiviral product may be formulated for use in inhalation therapy by coating the particles and micronizing the particles for inhalation.

In a preferred embodiment, the antiviral product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antiviral product. Thus, for example, antiviral products may include a first dosage form in the form of a tablet that is an immediate release tablet, and may also include two or more additional tablets, each of which provides for a delayed release of the antiviral, as hereinabove described, whereby the $C_{max}$ of the antiviral released from each of the tablets is reached at different times, with the $C_{max}$ of the total antiviral released from the antiviral product being achieved in less than twelve hours.

The formulation of an antiviral product including at least three dosage forms with different release profiles for different routes of administration is deemed to be within the skill of the art from the teachings herein. As known in the art, with respect to delayed release, the time of release can be controlled by the concentration of antivirals in the coating and/or the thickness of the coating.

In formulating an antiviral product in accordance with the invention, in one embodiment, the immediate release dosage form of the product generally provides from about 20% to about 50% of the total dosage of antiviral to be delivered by the product, with such immediate release dosage forms generally providing at least 25% of the total dosage of the antiviral to be delivered by the product. In many cases, the immediate release dosage form provides from about 20% to about 30% of the total dosage of antiviral to be delivered by the product; however, in some cases it may be desirable to have the immediate release dosage form provide for about 45% to about 50% of the total dosage of antiviral to be delivered by the product.

The remaining dosage forms deliver the remainder of the antiviral. If more than one delayed release dosage form is used, in one embodiment, each of the delayed release dosage forms may provide about equal amounts of antiviral; however, they may also be formulated so as to provide different amounts.

In accordance with the present invention, each of the dosage forms contains the same antiviral; however, each of the dosage forms may contain more than one antiviral.

In one embodiment, where the composition contains one immediate release component and two delayed release components, the immediate release component provides from 20% to 35% (preferably 20% to 30%), by weight, of the total antiviral; where there is three delayed release components, the immediate release component provides from 15% to 30%, by weight, of the total antiviral; and where there are four delayed release components, the immediate release component provides from 10% to 25%, by weight, of the total antiviral.

With respect to the delayed release components, where there are two delayed release components, the first delayed release component (the one released earlier in time) provides from 30% to 60%, by weight, of the total antiviral provided by the two delayed release components with the second delayed release component providing the remainder of the antiviral.

Where there are three delayed release components, the earliest released component provides 20% to 35% by weight of the total antiviral provided by the three delayed release components, the next in time delayed release component provides from 20% to 40%, by weight, of the antiviral provided by the three delayed release components and the last in time providing the remainder of the antiviral provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total antiviral provided by the four delayed release components.

The Immediate Release Component

The immediate release portion of this system can be a mixture of ingredients that breaks down quickly after administration to release the antiviral. This can take the form of either a discrete pellet or granule that is mixed in with, or compressed with, the other three components.

The materials to be added to the antivirals for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05-15% (W/W).

The non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4-20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose,hydroxypropylmethylcellulose,hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4-20% (W/W).

As hereinabove indicated, the units comprising the antiviral composition of the present invention can be in the form of discrete pellets or particles contained in the capsule, or particles embedded in a tablet or suspended in a liquid suspension.

The antiviral composition of the present invention may be administered, for example, by any of the following routes of administration: sublingual, transmucosal, transdermal, parenteral, etc., and preferably is administered orally. The composition includes a therapeutically effective amount of the antiviral, which amount will vary with the antiviral to be used, the disease or infection to be treated, and the number of times that the composition is to be delivered in a day. The composition is administered to a host in an amount effective for treating a viral infection.

The following are representative examples of some antivirals that may be used in the product of the invention: Acyclovir, Amantadine, Amprenavir, Cidofovir, Delavirdine, Didanosine, Famciclovir, Foscamet, Ganciclovir, Indinavir, Interferon, Lamivudine, Nelfinavir, Nevirapine, Palivizumab, Penciclovir, Ribavirin, Rimantadine, Ritonavir, Saquinavir, Stavudine, Trifluridine, Valacyclovir, Vidarabine, Zalcitabine, Zidovudine The invention will be further described with respect to the following examples; however, the scope of the invention is not limited thereby. All percentages in this specification, unless otherwise specified, are by weight.

ANTIVIRAL EXAMPLES

Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum over or forced-air oven. The product may be sieved or granulated, and compressed using a suitable tablet press, such as a rotary table press.

|  | Ingredient | Conc. (% W/W) |
| --- | --- | --- |
| Example 1: | Acyclovir | 65% (W/W) |
|  | Microcrystalline cellulose | 20 |
|  | Povidone | 10 |
|  | Croscarmellose sodium | 5 |
| Example 2: | Acyclovir | 55% (W/W) |
|  | Microcrystalline cellulose | 25 |
|  | Povidone | 10 |
|  | Croscarmellose sodium | 10 |

|  | Ingredient | Conc. (% W/W) |
|---|---|---|
| Example 3: | Acyclovir | 65% (W/W) |
|  | Microcrystalline cellulose | 20 |
|  | Hydroxypropylcellulose | 10 |
|  | Croscarmellose sodium | 5 |
| Example 4: | Acyclovir | 75% (W/W) |
|  | Polyethylene glycol 4000 | 10 |
|  | Polyethylene glycol 2000 | 10 |
|  | Hydroxypropylcellulose | 5 |
| Example 5: | Acyclovir | 75% (W/W) |
|  | Polyethylene glycol 8000 | 20 |
|  | Polyvinylpyrrolidone | 5 |
| Example 6: | Zidovudine | 65% (W/W) |
|  | Microcrystalline cellulose | 20 |
|  | Hydroxypropylcellulose | 10 |
|  | Croscarmellose sodium | 5 |
| Example 7: | Zidovudine | 75% (W/W) |
|  | Microcrystalline cellulose | 15 |
|  | Hydroxypropylcellulose | 5 |
|  | Croscarmellose sodium | 5 |
| Example 8: | Zidovudine | 75% (W/W) |
|  | Polyethylene glycol 4000 | 10 |
|  | Polyethylene glycol 2000 | 10 |
|  | Hydroxypropylcellulose | 5 |
| Example 9: | Zidovudine | 75% (W/W) |
|  | Polyethylene glycol 8000 | 20 |
|  | Polyvinylpyrrolidone | 5 |
| Example 10: | Valacyclovir | 65% (W/W) |
|  | Microcrystalline cellulose | 20 |
|  | Hydroxypropylcellulose | 10 |
|  | Croscarmellose sodium | 5 |
| Example 11: | Valacyclovir | 75% (W/W) |
|  | Microcrystalline cellulose | 15 |
|  | Hydroxypropylcellulose | 5 |
|  | Croscarmellose sodium | 5 |
| Example 12: | Valacyclovir | 75% (W/W) |
|  | Polyethylene glycol 4000 | 10 |
|  | Polytheylene glycol 2000 | 10 |
|  | Hydroxypropylcellulose | 5 |
| Example 13: | Cirpofloxacin | 75% (W/W) |
|  | Polyethylene glycol 8000 | 20 |
|  | Polyvinylpyrrolidone | 5 |
| Example 14: | Ribavirin | 75% (W/W) |
|  | Polyethylene glycol 4000 | 10 |
|  | Polyethylene glycol 2000 | 10 |
|  | Hydroxypropylcellulose | 5 |
| Example 15: | Ribavirin | 75% (W/W) |
|  | Polyethylene Glycol 4000 | 20 |
|  | Polyvinylpyrrolidone | 5 |

Non pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

|  | Ingredient | Conc. (% W/W) |
|---|---|---|
| Example 16: | Acyclovir | 65% (W/W) |
|  | Microcrystalline cellulose | 20 |
|  | Polyox | 10 |
|  | Croscarmellose sodium | 5 |
| Example 17: | Acyclovir | 55% (W/W) |
|  | Microcrystalline cellulose | 25 |
|  | Polyox | 10 |
|  | Glyceryl monooleate | 10 |
| Example 18: | Acyclovir | 65% (W/W) |
|  | Polyox | 20 |
|  | Hydroxypropylcellulose | 10 |
|  | Croscarmellose sodium | 5 |
| Example 19: | Zidovudine | 70% (W/W) |
|  | Polyox | 20 |
|  | Hydroxypropylcellulose | 5 |
|  | Croscarmellose sodium | 5 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

|  | Ingredient | Conc. (% W/W) |
|---|---|---|
| Example 20: | Acyclovir | 65% (W/W) |
|  | Microcrystalline cellulose | 20 |
|  | Cellulose Acetate Pthalate | 15 |
| Example 21: | Acyclovir | 55% (W/W) |
|  | Microcrystalline cellulose | 25 |
|  | Cellulose Acetate Pthalate | 10 |
|  | Hydroxypropylmethylcellulose | 10 |
| Example 22: | Acyclovir | 65% (W/W) |
|  | Polyox | 20 |
|  | Hydroxypropylcellulose pthalate | 10 |
|  | Eudragit L30D | 5 |
| Example 23: | Acyclovir | 40% (W/W) |
|  | Microcrystalline Cellulose | 40 |
|  | Cellulose Acetate Pthalate | 10 |
| Example 24: | Zidovudine | 70% (W/W) |
|  | Hydroxypropylcellulose pthalate | 15 |
|  | Croscarmellose sodium | 10 |
| Example 25: | Zidovudine | 75% (W/W) |
|  | Polyethylene glycol 2000 | 10 |
|  | Eudragit L 30D | 15 |
| Example 26: | Zidovudine | 40% (W/W) |
|  | Lactose | 50 |
|  | Eudgragit L 30D | 10 |
| Example 27: | Valacyclovir | 65% (W/W) |
|  | Microcrystalline Cellulose | 20 |
|  | Eudragit L 30D | 10 |
| Example 28: | Valacyclovir | 75% (W/W) |
|  | Microcrystalline Cellulose | 15 |
|  | Hydroxypropylcellulose pthalate | 10 |
| Example 29: | Valacyclovir | 80% (W/W) |
|  | Lactose | 10 |
|  | Eudragit L 30D | 10 |
| Example 30: | Valacyclovir | 70% (W/W) |
|  | Polyethylene glycol 4000 | 20 |
|  | Cellulose acetate pthalate | 10 |
| Example 31: | Ribavirin | 60% (W/W) |
|  | Polyethylene glycol 2000 | 10 |
|  | Lactose | 20 |
|  | Eudragit L 30D | 10 |
| Example 32: | Ribavirin | 70% (W/W) |
|  | Microcrystalline cellulose | 20 |
|  | Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

|  | Ingredient | Conc. (% W/W) |
|---|---|---|
| Example 33: | Acyclovir | 65% (W/W) |
|  | Ethylcellulose | 20 |
|  | Polyox | 10 |
|  | Hydroxypropylmethylcellulose | 5 |
| Example 34: | Acyclovir | 55% (W/W) |
|  | Lactose | 25 |
|  | Polyox | 10 |
|  | Glyceryl monooleate | 10 |
| Example 35: | Acyclovir | 70% (W/W) |
|  | Polyox | 20 |
|  | Hydroxypropylcellulose | 10 |
| Example 36: | Zidovudine | 75% (W/W) |
|  | Lactose | 15 |
|  | Hydroxypropylcellulose | 5 |
|  | Ethylcellulose | 5 |
| Example 37: | Zidovudine | 75% (W/W) |
|  | Polyethylene glycol 4000 | 10 |
|  | Lactose | 10 |
|  | Eudragit RL 30D | 5 |
| Example 38: | Zidovudine | 80% (W/W) |
|  | Polyethylene glycol 8000 | 10 |
|  | Hydroxypropylmethylcellulose | 5 |
|  | Eudragit RS 30D | 5 |
| Example 39: | Valacyclovir | 75% (W/W) |
|  | Hydroxyethylcellulose | 10 |
|  | Polyethylene glycol 4000 | 10 |
|  | Hydroxypropylcellulose | 5 |
| Example 40: | Valacyclovir | 75% (W/W) |
|  | Lactose | 10 |
|  | Povidone (PVP) | 10 |
|  | Polyethylene glycol 2000 | 5 |
| Example 41: | Ribavirin | 75% (W/W) |
|  | Polyethylene glycol 4000 | 10 |
|  | Povidone (PVP) | 10 |
|  | Hydroxypropylcellulose | 5 |
| Example 42: | Ribavirin | 75% (W/W) |
|  | Lactose | 15 |
|  | Polyethylene glycol 4000 | 5 |
|  | Polyvinylpyrrolidone | 5 |
| Example 43: | Zidovudine | 40% (W/W) |
|  | Eudragit S100 | 50 |
|  | Triethyl Citrate | 10 |
| Example 44: | Zidovudine | 50% (W/W) |
|  | Sureteric | 50 |
| Example 45: | Zidovudine | 50% (W/W) |
|  | Eudragit S100 | 45 |
|  | Triethyl Citrate | 5 |

Three Pulses

Example 46

1. Antiviral Matrix Pellet Formulation and Preparation Procedure (Immediate Release)

A. Pellet Formulation

The composition of the antiviral matrix pellets provided in Table 1.

TABLE 1

Composition of Antiviral Pellets

| Component | Percentage (%) |
|---|---|
| Antiviral | 50 |
| Avicel PH 101 | 20 |
| Lactose | 20 |
| PVP K29/32* | 10 |
| Purified Water |  |
| Total | 100 |

*PVP K29/32 was added as a 20% w/w aqueous solution during wet massing.

B. Preparation Procedure for Antiviral Matrix Pellets 1.2.1 Blend antiviral and Avicel® PH 101 using a Robot Coupe high shear granulator.
1.2.2 Add 20% Povidone K29/32 binder solution slowly into the powder blend under continuous mixing.
1.2.3 Extrude the wet mass using an LCI Bench Top Granulator. The diameter of the screen of the Bench Top Granulator was 1.0 mm.
1.2.4 Spheronize the extrudate using a Model SPH20 Caleva Spheronizer.
1.2.5 Dry the spheronized pellets at 50° C. overnight.
1.2.6 Pellets between 16 and 30 Mesh were collected for further processing.

1.3 Preparation of an Eudragit® L 30 D-55 Aqueous Coating Dispersion

A. Dispersion Formulation

The composition of the aqueous Eudragit L30D-55 dispersion applied to the antiviral matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion 1.3.1 Suspend triethyl citrate and talc in deionized water.
1.3.2 The TEC/talc suspension is then homogenized using a PowerGen 700 high shear mixer.
1.3.3 Add the TEC/talc suspension slowly to the Eudragit® L 30 D-55 latex dispersion while stirring.
1.3.4 Allow the coating dispersion to stir for one hour prior to application onto the antiviral matrix pellets.

1.4 Preparation of an Eudragit® S 100 Aqueous Coating Dispersion

A. Dispersion Formulation

The composition of the aqueous Eudragit® S 100 dispersion applied to the antiviral matrix pellets is provided below in Table 3.

TABLE 3

Eudragit® S 100 Aqueous Coating Dispersion

| Component | Percentage (%) |
|---|---|
| Part A | |
| Eudragit® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion

Part I:
(i) Dispense Eudragit® S 100 powder in deionized water with stirring.
(ii) Add ammonium hydroxide solution drop-wise into the dispersion with stirring.
(iii) Allow the partially neutralized dispersion to stir for 60 minutes.
(iv) Add triethyl citrate drop-wise into the dispersion with stirring. Stir for about 2 hours prior to the addition of Part B.

Part II:
(i) Disperse talc in the required amount of water
(ii) Homogenize the dispersion using a PowerGen 700D high shear mixer.
(iii) Part B is then added slowly to the polymer dispersion in Part A with a mild stirring.

1.5 Coating Conditions for the Application of Aqueous Coating Dispersions The following coating parameters are used to coat matrix pellets with each of the Eudragit® L 30 D-55 and Eudragit® S 100 aqueous film coating.

| | |
|---|---|
| Coating Equipment | STREA 1™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.

1.6 Encapsulation of the Antiviral Pellets

Pellets are filled into size 00 hard gelatin capsules at a ratio of 30%: 30%: 40%: Immediate-release matrix pellets uncoated, L30 D-55 coated pellets and S100 coated pellets respectively.

The capsule is filled with the three different pellets to achieve the desired dosage.

Three Pulses

Example 47

Antiviral Pellet Formulation and Preparation Procedure 47.1 Pellet Formulations for Subsequent Coating The composition of the Antiviral trihydrate matrix pellets provided in Table 4.

TABLE 4

Composition of Antiviral Matrix Pellets

| Component | Percentage (%) |
|---|---|
| Antiviral Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.2 Preparation Procedure for Antiviral Matrix Pellets 47.2.1 Blend Antiviral and Avicel® PH 101 using a low shear blender.

47.2.2 Add the hydroxypropyl methylcellulose binder solution slowly into the powder blend under continuous mixing.

47.2.3 Extrude the wet mass using an LCI Bench Top Granulator. The diameter of the screen of the Bench Top Granulator is 0.8 mm.

47.2.4 Spheronize the extrudate using a QJ-230 Spheronizer using a small cross section plate.

47.2.5 Dry the spheronized pellets at 60° C. using a fluid bed dryer until the exhaust temperature reaches 40° C.

47.2.6 Pellets between 20 and 40 Mesh were collected for further processing.

47.3 Preparation of an Eudragit® L 30 D-55 Aqueous Coating Dispersion 47.3.1 Dispersion Formulation The composition of the aqueous Eudragit L30D-55 dispersion applied to the antiviral matrix pellets is provided below in Table 5.

TABLE 5

Eudragit® L 30 D-55 Aqueous Coating Dispersion

| Component | Percentage (%) |
|---|---|
| Eudragit® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

47.4 Preparation Procedure for an Eudragit® L 30 D-55 Aqueous Dispersion 47.4.1 Suspend triethyl citrate and talc in deionized water.

47.4.2 The TEC/talc suspension is mixed using laboratory mixer.

47.4.3 Add the TEC/talc suspension from slowly to the Eudragit® L 30 D-55 latex dispersion while stirring.

47.4.4 Allow the coating dispersion to stir for one hour prior to application onto the antiviral matrix pellets.

47.5 Preparation of an Eudragit® S 100 Aqueous Coating Dispersion 47.5.1 Dispersion Formulation The composition of the aqueous Eudragit® S 100 dispersion applied to the Antiviral matrix pellets is provided below in Table 6.

TABLE 6

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

47.6 Preparation Procedure for an Eudragit® S 100 Aqueous Dispersion

Part A:

47.6.1 Dispense Eudragit® S 100 powder in deionized water with stirring.

47.6.2 Add ammonium hydroxide solution drop-wise into the dispersion with stirring.

47.6.3 Allow the partially neutralized dispersion to stir for 60 minutes.

47.6.4 Add triethyl citrate drop-wise into the dispersion with stirring and let stir overnight prior to the addition of Part B.

Part B:

47.6.5 Disperse talc in the required amount of water 47.6.6 Stir the dispersion using an overhead laboratory mixer.

47.6.7 Part B is then added slowly to the polymer dispersion in Part A with a mild stirring.

47.7 Coating Conditions for the Application of Aqueous Coating Dispersions

The following coating parameters are used for both the Eudragit® L 30 D-55 and Eudragit® S 100 aqueous film coating processes.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2–6 gram per minute |

47.7.1 Coat matrix pellets with L30 D-55 dispersion such that you apply 20% coat weight gain to the pellets.

47.7.2 Coat matrix pellets with S100 dispersion such that you apply 37% coat weight gain to the pellets.

47.8 Preparation of Antiviral Granulation (Immediate Release Component) for tabletting

TABLE 7

Composition of Antiviral Granulation

| Component | Percentage (%) |
|---|---|
| Antiviral Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.8.1 Blend Antiviral and Avicel® PH 101 using a low shear blender.

47.8.2 Add the hydroxypropyl methylcellulose binder solution slowly into the powder blend under continuous mixing.

47.8.3 Dry the granulation at 60° C. using a fluid bed dryer until the exhaust temperature reaches 40° C.

47.8.4 Granules between 20 and 40 Mesh are collected for further processing.

47.9 Tabletting of the Antiviral Pellets

TABLE 8

Composition of Antiviral Tablets

| Component | Percentage (%) |
|---|---|
| Antiviral granules | 32.5 |
| Avicel PH 200 | 5.0 |
| Antiviral L30D-55 coated pellets | 30 |
| Antiviral S100 coated pellets | 30 |
| Colloidal silicon dioxide | 1.5 |
| Magnesium stearate | 1.0 |
| Total | 100 |

47.9.1 Blend the Antiviral granules, Avicel PH-200, Antiviral pellets and colloidal silicon dioxide for 15 minutes in a tumble blender.

47.9.2 Add the magnesium stearate to the blender, and blend for 5 minutes.

47.9.3 Compress the blend on a rotary tablet press.

47.9.4 The fill weight should be adjusted to achieve the desired dosage.

Four pulses

Example 48

1 Antiviral Matrix Pellet Formulation and Preparation Procedure 48.1 Pellet Formulation The composition of the antiviral matrix pellets provided in Table 9.

TABLE 9

Composition of Antiviral Pellets

| Component | Percentage (%) |
|---|---|
| Antiviral | 50 |
| Avicel PH 101 | 20 |
| Lactose | 20 |

TABLE 9-continued

Composition of Antiviral Pellets

| Component | Percentage (%) |
|---|---|
| PVP K29/32* | 10 |
| Purified Water | |
| Total | 100 |

*PVP K29/32 was added as a 20% w/w aqueous solution during wet massing.

48.2 Preparation Procedure for Antiviral Matrix Pellets 48.2.1 Blend antiviral and Avicel® PH 101 using a Robot Coupe high shear granulator.

48.2.2 Add 20% Povidone K29/32 binder solution slowly into the powder blend under continuous mixing.

48.2.3 Extrude the wet mass using an LCI Bench Top Granulator. The diameter of the screen of the Bench Top Granulator was 1.0 mm.

48.2.4 Spheronize the extrudate using a Model SPH20 Caleva Spheronizer.

48.2.5 Dry the spheronized pellets at 50° C. overnight.

48.2.6 Pellets between 16 and 30 Mesh were collected for further processing. ps 48.3 Preparation of an Eudragit® L 30 D-55 Aqueous Coating Dispersion 48.3.1 Dispersion Formulation The composition of the aqueous Eudragit L30D-55 dispersion applied to the antiviral matrix pellets is provided below in Table 10.

TABLE 10

Eudragit® L 30 D-55 Aqueous Coating Dispersion

| Component | Percentage (%) |
|---|---|
| Eudragit® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

48.4 Preparation Procedure for an Eudragit® L 30 D-55 Aqueous Dispersion 48.4.1 Suspend triethyl citrate and talc in deionized water.

48.4.2 The TEC/talc suspension is then homogenized using a PowerGen 700 high shear mixer.

48.4.3 Add the TEC/talc suspension slowly to the Eudragit® L 30 D-55 latex dispersion while stirring.

48.4.4 Allow the coating dispersion to stir for one hour prior to application onto the antiviral matrix pellets.

48.5 Preparation of an Eudragit® S 100 Aqueous Coating Dispersion 48.5.1 Dispersion Formulation The composition of the aqueous Eudragit® S 100 dispersion applied to the antiviral matrix pellets is provided below in Table 11.

TABLE 11

Eudragit® S 100 Aqueous Coating Dispersion

| Component | Percentage (%) |
|---|---|
| Part A | |
| Eudragit® S 100 | 12.0 |
| 1 N Ammonium Hydroxide | 6.1 |

TABLE 11-continued

Eudragit® S 100 Aqueous Coating Dispersion

| Component | Percentage (%) |
|---|---|
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

48.6 Preparation Procedure for an Eudragit® S 100 Aqueous Dispersion

Part A:

48.6.1 Dispense Eudragit® S 100 powder in deionized water with stirring.

48.6.2 Add ammonium hydroxide solution drop-wise into the dispersion with stirring.

48.6.3 Allow the partially neutralized dispersion to stir for 60 minutes.

48.6.4 Add triethyl citrate drop-wise into the dispersion with stirring. Stir for about 2 hours prior to the addition of Part B.

Part B:

48.6.5 Disperse talc in the required amount of water 48.6.6 Homogenize the dispersion using a PowerGen 700D high shear mixer.

48.6.7 Part B is then added slowly to the polymer dispersion in Part A with a mild stirring.

48.7 Coating Conditions for the Application of Aqueous Coating Dispersions

The following coating parameters are used for coating with each of the Eudragit® L 30 D-55 and Eudragit® S 100 aqueous film coatings.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

48.7.1 Coat matrix pellets with L30 D-55 dispersion such that you apply 12% coat weight gain to the pellets.

48.7.2 Coat matrix pellets with L30 D-55 dispersion such that you apply 30% coat weight gain to the pellets.

48.7.3 Coat matrix pellets with S100 dispersion such that you apply 20% weight gain to the pellets.

48.8 Encapsulation of the Antiviral Pellets

Pellets are filled into size 00 hard gelatin capsules at a ratio of 20%: 30%: 20%: 30% Immediate-release matrix pellets (uncoated), L30 D-55 coated pellets 12% weight gain, L30D-55 coated pellets 30% weight gain and S100 coated pellets respectively. The capsule is filled with the four different pellets to achieve the desired dosage.

The present invention is particularly advantageous in that there is provided an antiviral product which provides an improvement over twice a day administration of the antiviral and an improvement over a once a day administration of the antiviral.

Numerous modification and variations of the present invention are possible in light of the above teachings and therefore, within the scope of the appended claims the invention may be practiced otherwise than as particularly described.

What is claimed is:

1. A once-a-day antiviral product comprising: first, second, and third antiviral dosage forms, each of said antiviral dosage forms comprising at least one antiviral and a pharmaceutically acceptable carrier, said first antiviral dosage form being an immediate release dosage form, said second and third antiviral dosage forms being delayed release dosage forms wherein at least one of said second or third dosage forms is a non-pH sensitive dosage form, and wherein each of said first, second, and third antiviral dosage forms initiates release at different times and Cmax in serum of the total antiviral released from said antiviral product is achieved in less than about 12 hours from administration and said once-a-day antiviral product contains the total dosage of the at least one antiviral for a twenty-four hour period.

2. The product of claim 1, wherein the Cmax for the product is reached no earlier than four hours after administration.

3. The product of claim 1, wherein the antiviral released from the first dosage form reaches a Cmax within from about 0.5 hours to about 2 hours after administration of the product.

4. The product of claim 1, wherein the antiviral released from the second dosage form reaches a Cmax in no more than about 4 hours after administration of the product.

5. The product of claim 1, wherein the antiviral released from the third dosage form reaches a Cmax within 8 hours after administration of the product.

6. The product of claim 1, wherein the immediate release dosage form contains at least 20% and no more than 50% of the total dosage of antiviral.

7. The product of claim 1, wherein the product is an oral dosage form.

8. The product of claim 7, wherein the antiviral released from the second dosage form reaches a Cmax after Cmax is reached for the antiviral released from the first dosage form.

9. The product of claim 8, wherein the antiviral released from the third dosage form reaches a Cmax after Cmax is reached for the antiviral released from the second dosage form.

10. The product of claim 1, wherein said second dosage form initiates release of said antiviral before said third dosage form, wherein said second dosage form provides from 30% to 60% by weight of the total antiviral released by said second and third dosage forms, and wherein said third dosage form provides the remainder of the total antiviral released by said second and third dosage forms.

11. The product of claim 1 further comprising a fourth antiviral dosage form, said fourth antiviral dosage form comprising at least one antiviral and a pharmaceutically acceptable carrier and wherein said at least one antiviral released from said fourth antiviral dosage form reaches a Cmax in the serum after Cmax is achieved in the serum for antiviral released from each of said first, second, and third dosage forms.

12. The product of claim 11, wherein said fourth antiviral dosage form is a delayed release dosage form.

13. The product of claim 11, wherein the Cmax for the product is reached no earlier than four hours after administration.

14. The product of claim 11, wherein the antiviral released from the first dosage form reaches a Cmax within from about 0.5 hours to about 2 hours after administration of the product.

15. The product of claim 11, wherein the antiviral released from the second dosage form reaches a Cmax in no more than about 4 hours after administration of the product.

16. The product of claim 11, wherein the antiviral released from the third dosage form reaches a Cmax within 8 hours after administration of the product.

17. The product of claim 11, wherein said second dosage form initiates release of antiviral before said third dosage form, wherein said third dosage form initiates release of antiviral before said fourth dosage form, wherein said second dosage form provides 20% to 35% by weight of the total antiviral released by said second, third, and fourth dosage forms, wherein said third dosage form provides from 20% to 40% by weight of the total antiviral released by said second, third, and fourth dosage forms, and wherein said fourth dosage form provides the remainder of the total antiviral released by said second, third, and fourth dosage forms.

18. The product of claim 11, wherein the product is an oral dosage form.

19. The product of claim 11, wherein the antiviral released from the second dosage form reaches a Cmax after Cmax is reached for the antiviral released from the first dosage form.

20. The product of claim 11, wherein the antiviral released from the third dosage form reaches a Cmax after Cmax is reached for the antiviral released from the second dosage form.

21. A process for treating a viral infection in a host comprising: administering to a host the antiviral product of claim 1, once-a-day.

22. A process for treating a viral infection in a host comprising: administering to a host the antiviral product of claim 2, once-a-day.

23. A process for treating a viral infection in a host comprising: administering to a host the antiviral product of claim 3, once-a-day.

24. A process for treating a viral infection in a host comprising: administering to a host the antiviral product of claim 4, once-a-day.

25. A process for treating a viral infection in a host comprising: administering to a host the antiviral product of claim 5, once-a-day.

26. A process for treating a viral infection in a host comprising: administering to a host the antiviral product of claim 6, once-a-day.

27. A process for treating a viral infection in a host comprising: administering to a host the antiviral product of claim 7, once-a-day.

28. A process for treating a viral infection in a host comprising: administering to a host the antiviral product of claim 8, once-a-day.

29. A process for treating a viral infection in a host comprising: administering to a host the antiviral product of claim 9, once-a-day.

30. A process for treating a viral infection in a host comprising: administering to a host the antiviral product of claim 10, once-a-day.

31. A process for treating a viral infection in a host comprising: administering to a host the antiviral product of claim 11, once-a-day.

32. A process for treating a viral infection in a host comprising: administering to a host the antiviral product of claim 12, once-a-day.

33. A process for treating a viral infection in a host comprising: administering to a host the antiviral product of claim 13, once-a-day.

34. A process for treating a viral infection in a host comprising: administering to a host the antiviral product of claim 14, once-a-day.

35. A process for treating a viral infection in a host comprising: administering to a host the antiviral product of claim 15, once-a-day.

36. A process for treating a viral infection in a host comprising: administering to a host the antiviral product of claim 16, once-a-day.

37. A process for treating a viral infection in a host comprising: administering to a host the antiviral product of claim 17, once-a-day.

38. A process for treating a viral infection in a host comprising: administering to a host the antiviral product of claim 18, once-a-day.

39. A process for treating a viral infection in a host comprising: administering to a host the antiviral product of claim 19, once-a-day.

40. A process for treating a viral infection in a host comprising: administering to a host the antiviral product of claim 20, once-a-day.

41. The once-a-day antiviral product of claim 1, wherein the antiviral is in the form of a salt.

42. A process for treating a viral infection in a host comprising: administering to a host the antiviral product of claim 41, once-a-day.

43. A process for treating a patient with an antiviral agent said process for treating comprising:

administering to a patient once-a-day an antiviral product, said product comprising: first, second, and third dosage forms, wherein each of said dosage forms includes at least one antiviral agent and a pharmaceutically acceptable carrier; said treating including an immediate release of antiviral agent from said first dosage form and delayed releases of antiviral agent from each of said second and third dosage forms, wherein at least one of said second or third dosage forms is a non-pH sensitive dosage form, said immediate release and two delayed releases initiating release of antiviral agent at different times to produces a Cmax in serum of the total antiviral agent released from said antiviral product in less than about 12 hours from administration; and said treating delivers the total dosage of said at least one antiviral agent for a twenty-four hour period.

44. A once-a-day antiviral product comprising: first, second, and third antiviral dosage forms, each of said antiviral dosage forms comprising at least one antiviral agent and a pharmaceutically acceptable carrier, said first antiviral dosage form being an immediate release dosage form, said second and third antiviral dosage forms being delayed release dosage forms, wherein each of said second and third delayed release dosage forms comprise an immediate release dosage form and a member independently selected from the group consisting of: pH-sensitive components and non-pH-sensitive components to delay the release of the antiviral agent, wherein each of said first, second, and third antiviral dosage forms initiates release at different times, wherein Cmax in serum of the total antiviral agent released from said antiviral product is achieved in less than about 12 hours from administration, and said once-a-day antiviral product contains the total dosage of the at least one antiviral agent for a twenty-four hour period.

45. A process for treating a viral infection in a host comprising: administering to a host the antiviral product of claim 44 once-a-day.

* * * * *